US006187800B1

(12) United States Patent
Suri et al.

(10) Patent No.: US 6,187,800 B1
(45) Date of Patent: Feb. 13, 2001

(54) METHOD FOR THE PREVENTION AND TREATMENT OF MASTITIS

(75) Inventors: Bruno Suri, Bubendorf; Catherine Georges, Aesch; John Edmondson Peel, Seiry, all of (CH)

(73) Assignee: Novartis Animal Health U.S., Inc., Greensboro, NC (US)

( * ) Notice: Under 35 U.S.C. 154(b), the term of this patent shall be extended for 0 days.

(21) Appl. No.: 09/202,650

(22) PCT Filed: Jun. 19, 1997

(86) PCT No.: PCT/EP97/03212

§ 371 Date: Dec. 18, 1998

§ 102(e) Date: Dec. 18, 1998

(87) PCT Pub. No.: WO97/48408

PCT Pub. Date: Dec. 24, 1997

(30) Foreign Application Priority Data

Jun. 20, 1997 (DE) .................................................. 96810415

(51) Int. Cl.[7] ..................... A01N 43/78; A61K 31/425; A61K 35/00; A23C 9/12
(52) U.S. Cl. ..................... 514/366; 514/365; 514/359; 424/116; 424/118; 426/34; 426/36
(58) Field of Search ..................................... 514/366, 365, 514/359; 426/36, 34, 116, 118

(56) References Cited

FOREIGN PATENT DOCUMENTS

95/05844    3/1995    (WO) .

OTHER PUBLICATIONS

Eberhart. Veterinary Clinics of North America: Large Animal Practice, vol. 6, No. 2, 287–300, Jul. 1984.*
Rosendahl et al. Nucleic Acids Research, vol. 22, No. 3, 357–363, 1994.*
Cundliffe et al. Eur. J. Biochem., vol. 118, pp. 47–52, 1981.*
The Merck Index, S. Budavari et al., Editors, 11th Edition, p. 972, Monograph No. 6103 (1989), USA XP002018736.
Nature, vol. 178, pp. 44–45, E.P. Abraham et al. (Jul. 7, 1956), XP 002043055.
J.C.S. Chem. Comm., No. 6, pp. 256–258, (Mar. 15, 1978), XP002043056.
Antibiotics and Chemotheraphy, vol. 10, No. 7, J.D. Levin et al., pp. 422–429 (Jul. 1960), XP002018735.

* cited by examiner

Primary Examiner—Francisco Prats
Assistant Examiner—Susan D. Coe
(74) Attorney, Agent, or Firm—Michael P. Morris; William A. Teoli, Jr.

(57) ABSTRACT

A method for treating or preventing mastitis in mammals is disclosed. The method contemplates the intramammary injection or dipping the teat with micrococcin antibiotics, preferably micrococcin P1 or P2, which do not interfere with the production of cheese and yoghurt using milk from treated animals. Hydrophobic antibiotics such as micrococcin P1 or P2 can be administered prior to infection to effectively suppress the rate, severity, and duration of subsequent bacterial infection, or can be administered subsequent to infection to effectively treat mastitis.

9 Claims, No Drawings

METHOD FOR THE PREVENTION AND TREATMENT OF MASTITIS

The present invention relates to a method for treating or preventing mastitis in mammals. Said method embraces the intramammary injection or dipping the teat with micrococcin antibiotics, preferably micrococcin P1 or P2, which do not interfere with the production of cheese and yoghurt using milk from treated animals. Hydrophobic antibiotics such as micrococcin P1 or P2 can be administered prior to infection to effectively suppress the rate, severity, and duration of subsequent bacterial infection, or can be administered subsequent to infection to effectively treat mastitis. In particular, the invention describes the use of micrococcin P1 or P2 for the preparation of a drug to prevent bovine mastitis.

Mastitis is an inflammatory disease of the mammalian mammary gland. In veterinary medicine mastitis is most frequently encountered in dairy cows which are highly specialised for milk production. This specialisation, and the convention of milking dairy cows 2 or at most 3 times during 24 hours, renders their mammary glands susceptible to bacterial infections. Though the mammary gland has a number of natural defense mechanisms against bacterial pathogens (Cullor et al., 1990), these mechanisms are frequently overcome by high levels of bacterial exposure.

Milking, for example, is usually done by a mechanical apparatus which passes from cow to cow and thus increases the risk of transmitting an infection from one animal to another. Additionally, physiological changes at certain times in the lactation cycle result in compromise of the natural defense mechanism (Cullor et al., 1990). The periods around drying off and calving are associated with a high incidence of mastitis.

Mastitis can be caused by many different species of bacteria. Those most commonly implicated in bovine mastitis are either host pathogens such as *Staphylococcus aureus* and *Streptococcus agalactiae* or environmental pathogens such as *Streptococcus uberis* and *Escherichia coli*. Host pathogens live on the skin of the udder or in the udder and individual cows are the source of infection to others in the herd. Environmental pathogens on the other hand are found in the immediate environment of the dairy cow and present a constant risk (Cullor et al., 1990).

Mastitis caused by the bacteria characterized above can manifest as either clinical or subclinical disease (Cullor et al., 1990).

Clinical disease varies from mildly affected quarters with changes in the milk through severely infected quarters with eventual loss of that quarter, to systemically ill cows that may die. Milder manifestations are more usual.

Subclinical mastitis is prevalent in many dairy herds. Affected quarters are infected with the pathogenic bacteria described above, but clinical signs are absent. The level of somatic cells increases in the milk. This change can only be detected by specific test procedures known in the art. The syndrome is accompanied by lowered milk production and milk quality. It has been estimated that up to 70% of the economic losses sustained by farmers as a result of mastitis can be attributed to lost production caused by subclinical disease (Philpot, W.N., 1984).

Currently mastitis is controlled through the exercise of scrupulous hygiene at milking, or by detection of subclinically infected cows. These are then milked after the non-infected cows or may even be eliminated from the herd.

Clinical cases of mastitis are generally treated with commercially available antibiotic preparations such as Ampiclox™, Kloxerate plus™, Mastijet™, Tetra delta™, and Synulox™. The use of these preparations requires withholding of the milk from sale, because of the antibiotic residues present. The withholding times vary from 4–8 milkings depending on individual preparations. This is a cause of economic loss to the farmer. To avoid these losses antimicrobial therapy of subclinical mastitis is frequently postponed to the dry period. However, during the period between establishment of infection and drying off the infected cow is a risk to her neighbours. Reduction of bacterial numbers in infected quarters as a result of antibiotic treatment helps to reduce the spread of infection. It also improves the quality of milk, which is rewarded by premium payments in many countries. Thus, the goal of treatment during lactation is to attain a maximum cure consistent with a minimum treatment, and milk discard time, and with a rapid return to normal production of good quality milk.

The use of antibiotics, for the treatment of mastitis during lactation, raises another problem. The production of cheese and yoghurt is based on the bacterial fermentation of milk, and these processes are usually upset by residual antibiotics in the milk. Therefore, the milk of animals during treatment with antibiotics, and the milk from several milkings after the treatment has ended, cannot be used for the production of cheese and yoghurt.

The present invention for the first time describes the antibiotics micrococcin P1 or P2 which when used for the preparation of a drug to treat or prevent mastitis do not interfere with the production of cheese and yoghurt using milk from treated animals such as cows, goats or ewes. Surprisingly, the antibiotics according to the invention are highly hydrophobic and thus poorly soluble in water. In particular, the present invention describes the use of micrococcin P1 or P2 in drugs for the treatment of bovine mastitis. Pharmaceutically acceptable acid addition salts of these antibiotics may also be used.

In a preferred embodiment of the present invention micrococcin P1 or P2 are used to prepare a drug for treating or preventing mastitis. These antibiotics are shown to be highly active against pathogens causing bovine mastitis. What is even more important they can be used to treat or prevent mastitis without interfering with cheese and yoghurt production. This is not the case for conventionally employed antibiotics.

The chemical structure of the micrococcins P1 and P2 is described in Bycroft et al, 1978 and in the CRC Handbook of Antibiotic Compounds, pages 389–417. They are microbial products which can be purified from certain microorganisms such as for example *Staphylococcus sciuri*. For this purpose the microorganisms are harvested by centrifugation, and the micrococcins are extracted from the cell pellet using suitable solvents such as pure methanol, ethanol or chloroform. The extract is then subjected to standard chromatographic purification procedures to isolate pure micrococcin P1 or P2.

Another embodiment of the present invention is directed to a method of treating or preventing mastitis in a mammal, comprising administration to said mammal of a therapeutically effective amount of a micrococcin antibiotic which does not interfere with the production of cheese and yoghurt using milk from treated animals. Such a method avoids withholding milk from mammals that have received therapeutic or prophylactic doses of an antibiotic to treat or prevent mastitis. Thus the milk obtained from treated animals can be used in methods for the production of cheese and yoghurt.

The main aspect of the present invention is the treatment or prevention of mastitis in mammals such as cows, goats or ewes. By "treating" is meant curing or ameliorating the disease in an animal that has contracted mastitis. "Preventing" mastitis means preventing the occurrence of the infection, or tempering the severity of the infection if it is later contracted.

The active agents of the present invention are usually prepared and stored as ready-to-use liquid formulations. The solutions are generally applicable, but the formulation can be adapted to the specific type of administration. Thus the formulation can also contain non-ionic surfactants that carry no discrete charge when dissolved, and are selected from ethoxylated esters of fatty acids and triglycerides. The formulation may also contain EDTA to improve the antimicrobial spectrum and stabilizing agents such as methionines, ascorbic acid, and preservatives such as propylene glycol.

Typically, the active agents of the present invention are administered by intramammary injection. However, effective dosages may be also be administered by teat dipping or by parenteral or oral routes. The active agent may be administered prior to infection, and thus serve as a prophylactic. Administration during the prepartum or postpartum period is possible. In a preferred embodiment of the present invention the administration is carried out via intramuscular, subcutaneous, or intravenous injection. When prepared as injectables, the active agents according to the present invention are generally administered using a pharmaceutically acceptable vehicle or excipient. Suitable vehicles are, for example, water, saline, mannitol, dextran, amino acids, glycerol, or the like, in various combinations. In addition, if desired, the vehicle may contain auxiliary substances such as wetting or emulsifying agents, preservatives and pH buffering agents. The active ingredient will typically range from about 1% to about 95% (w/w) of the pharmaceutical composition administered, or even higher or lower if appropriate.

Parenteral administration may be conventionally accomplished by intradermal, subcutaneous, intramuscular, and even intravenous injection. Needle-less air-blast injection devices may be equally useful. Parenteral administration is well known in the art and may be carried out in ways common in the animal veterinary or human medical art.

Sustained action of the active agent to achieve prolonged release (so called 'slow release') can be obtained by formulating the active agent in a matrix that will physically inhibit rapid dissolution. The formulated matrix is injected into the animal's body where it remains as a depot from which the protein is slowly released. Useful adjuvants in this respect are polymers and copolymers of lactides and glycosides. Furthermore, gelling agents like aluminum, calcium or magnesium monostearate, or carbohydrates (cellulose, pectin, dextran derivatives), polysiloxanes or proteins (gelatin, collagen) may be used to extend the releasing time of the active agents of the present invention after parenteral application. Percutaneous administration is also meant to include implantation of controlled release devices. Such devices, made from silicone or wax or other polymeric matrices can be used subcutaneously to deliver the compound over the required period of time. This can also be achieved by implantation of minipumps containing solutions of the active agent. Such implantation techniques are well known in the art and often used in medical treatment.

Polysiloxane carriers are described in the art for a variety of hormonal delivery forms and may be adapted to the release of the active agents of the present invention. A collagen delivery system for the release of antibiotics is described in the German Offenlegungsschrift DE-3,429,038. This system can also be adapted for the present invention.

Slow release formulations and other pharmaceutical or veterinary formulations can be prepared by adapting peptide and protein formualtions already described in the art.

A "therapeutically effective amount" of an active agent of the present invention is a dose sufficient to either prevent or treat mastitis in a subject to which the active agent is administered. The dosages of the active agents of the present invention which can treat or prevent mastitis can be determined in view of this disclosure by one of ordinary skill in the art by running routine trials with appropriate controls. Comparison of the appropriate treatment groups to the controls will indicate whether a particular dosage is effective in preventing or treating a disease used in a controlled challenge. In general, effective dosage will vary depending on the mode of administration and action. It has been found that in the case of an intramammary injection using micrococcin administration of a dose in the range from 0.1 mg per quarter to 200 mg per quarter, preferably from 0.5 mg per quarter to 10 mg per quarter and most preferable from 1 mg per quarter to 4 mg per quarter is sufficient to control mastitis due to *Staphylococcus aureus*.

If administered intramuscularly, subcutaneously, or intravenously, effective dosages will depend on the weight of the animal and will typically run in the range of from about 0.1 mg/kg to about 200 mg/kg. More typically, the dosage will be at least about 0.5 mg/kg, but less than 150 mg/kg.

Beyond dosage, effective administration of an active agent according to the present invention will in part depend on the number and timing of the dosages. For example, multiple administrations of a dosage may be required. They are given to an animal about 6 to 72 hours apart, and preferably about 12 hours apart. In most circumstances it may be desirable to administer the active agent at least twice. It may even be desirable to administer more dosages to the animal, such as three, four, five, six, seven, eight, nine, ten or even up to 15 dosages. Again, it is believed that the precise combination of dosage and timing will be subject to a wide range of variation and that numerous combinations effective in treating or preventing a disease can be readily established by those of ordinary skill in the art in view of the present disclosure.

The invention now being fully described, it will be apparent to one of ordinary skill in the art, that many changes and modifications can be made thereto without departing from the spirit or scope of the appended claims.

Described below are several examples illustrating the practice of the present invention. These examples are provided for illustrative purposes only, and are not intended to limit the scope of the appended claims.

EXPERIMENTAL

Example 1

Purification of micrococcin P1

Cultures of *Staphylococcus sciuri* are grown according to standard techniques. At the end of fermentation the whole fermentation broth is sterilized and the cells are harvested by centrifugation. The cell pellet is washed with 6 ml of 10 mM phosphate buffer, pH 7.0, for each gram cells. Micrococcin is extracted from the cell pellet by washing with pure methanol (3 ml per gram cells). The cells are then removed by centrifugation and discarded; the crude methanol extract is dried using a Rotavap. The dried solid extract is redissolved in the smallest possible volume of dichloromethane:methanol (95:5) and loaded onto a silicagel chromatography column (100 g silicagel per gram of dried solid extract). Micrococcin P1 is eluted from the column with dichloromethane:methanol (95:5). The presence of micrococcin P1 is visualized by thin layer chromatography using silicagel 60 $F_{254}$ plates and and dichloromethane:methanol (90:10) as the mobile phase. The fractions containing micrococcin P1 are pooled and dried using using the Rotavap. The dry material is then redissolved in 70% methanol to make up a concentration of 10 mg/ml. Water is added until the solubility limit is reached. The solution is loaded onto a Source 15 RPC (Pharmacia) column (9 ml gel per 100 g micrococcin P1). The column is equilibrated with 10% acetonitrile in 0.1% TFA. After loading the column is washed with equilibartion buffer and subjected to an acetonitrile gradient. Micrococcin P1 is eluted between 30%–50% acetonitrile in 0.1% TFA. The fractions containing micrococcin P1 are pooled and lyophilized.

Example 2

Antimicrobial spectrum of micrococcin P1

The minimal inhibitory concentrations (MIC) of micrococcin P1 against a panel of test organisms were determined using an agar well diffusion method. Agar plates were overlaid with soft agar seeded with the test organism. When the agar had solidified wells of 4 mm diameter were cut in the agar. 50 $\mu$l of a series of two fold dilutions of the peptide in citrate buffer pH4 were applied to the wells and the plates were kept at 4° C. for two hours prior to incubation at 37° C. overnight. The MIC was determined as the lowest concentration of peptide giving a clear zone of lysis around the well. Indicator strains were grown in Tryptose broth (Difco). M17 medium (Merck) was used for plates and soft agar with the following exceptions. For Pasteurella haemolytica, tryptose supplemented with 5% of toetal calf's serum was used. For Leuconostoc mesenteroides, plate count agar—Merck—, +15% saccharose was used, and for Bacillus cereus plate count agar +0.2% potato starch-Sigma 2004-) was used. Results are shown in Table 1.

TABLE 1

Activity Spectrum of mocrococcin P1 (MICS in $\mu$g/ml)

| Strain | MIC ($\mu$g/ml) |
| --- | --- |
| Staphylococcus aureus V557 | 1.91 |
| Staphylococcus aureus Newbould | 0.24 |
| Streptococcus uberis | 1.49 |
| Streptococcus faecalis | 1.98 |
| E.coli | >1000 |
| Pasteurella haemolytica | >1000 |
| Listeria innocua | 1.95 |
| Bacillus cereus | 0.24 |
| Micrococcus luteus | 0.015 |
| Leuconostoc mesenteroides | >1000 |

Example 3

Experiments evaluating the potential of micrococcin P1 in subclinical bovine mastitis A dairy herd is maintained to supply candidate cows for enrollment in trials. Cows are bought from local cattle dealers. These cows should have a minimal milk production of 15 l/day. Two milk samples are taken one day apart from all quarters for bacteriological examination. No cows from which mastitis pathogens can be recovered are entered into the tests. Non-infected cows are selected based on non recovery of Staphylococcus aureus from two milk samples taken one day apart from all quarters. Then, 3 quarters are inoculated via the intramammary route using a suspension of Staphylococcus aureus. The 4th quarter serves as a control for the milking hygiene routines. During the two to four weeks after inoculation, milk samples are taken from all quarters, at least 3 times. These samples are cultured, and if Staphylococcus aureus is recovered from at least two of them, the quarter is considered infected.

Treatments are assigned randomly to infected quarters and injected via the intramammary route. Milk samples are taken daily until a minimum of 14 days after the last treatment. A quarter is considered to be cured if milk samples from that quarter become negative (i.e., no Staphylococcus aureus can be recovered) within 7 days after the last treatment and stay negative throughout the following 14 day sampling period.

This experimental model is used to have a fixed framework on which to evaluate treatments. To work with Staphylococcus aureus has the advantage that it is the most difficult Gram positive bacterium to treat and one of the most important bacteria causing bovine mastitis. Therefore, cure rates should be expected to be lower than for other Gram positive bacteria, such as Streptococci and coagulase-negative Staphylococci.

This model has proved satisfactory since the infection rate in quarters averaged 60%, or 2 quarters/cow.

The results presented in Table 2 show the percentage of quarters positive for Staphylococcus aureus (i.e., quarters from which Staphylococcus aureus can be recovered) during and after treatment with 3 doses of either placebo, 2 mg micrococcin P1, or 300 mg ampiclox at 12 hour intervals, or 3 doses with 4 mg micrococcin P1 at 48 hour intervals.

TABLE 2

Summary of results of preliminary efficacy trials

Treatment Group

| days after start of treatment | 3 × placebo (no antibiotic) each 12 hours % of quarters positive (n = 45) | 3 × 2 mg micrococcin P1 each 12 hours % of quarters positive (n = 9) | 3 × 4 mg micrococcin P1 each 48 hours % of quarters positive (n = 9) | 3 × 300 mg ampiclox each 12 hours % of quarters positive (n = 68) |
| --- | --- | --- | --- | --- |
| 0 | 97.7 | 100.0 | 100 | 100 |
| 1 | 75.6 | 62.5 | 22 | 19 |
| 2 | 77.8 | 12.5 | 22 | 1 |
| 3 | 80.0 | 50.0 | 11 | 7 |
| 4 | 73.3 | 50.0 | 11 | 6 |
| 5 | 77.8 | 62.5 | 0 | 24 |
| 7 | 75.6 | 62.5 | 0 | 29 |
| 8 | 75.6 | 75.0 | 22 | 34 |
| 9 | 71.1 | 75.0 | 22 | 35 |
| 10 | 75.6 | 75.0 | 22 | 35 |
| 11 | 71.1 | 87.5 | 22 | 43 |
| 12 | 64.4 | 75.0 | 22 | 41 |
| 14 | 68.9 | 87.5 | 44 | 43 |
| 15 | 80.0 | 62.5 | 44 | 43 |
| 16 | 80.0 | 75.0 | 22 | |

Example 4

Teat Dipping and Mastitis Prophylaxis

Teat dipping is one of the most frequently used and most effective measures taken to prevent mastitis in dairy cows. All the teats of all cows are dipped in an antibacterial solution after every milking. The film of antibacterial agent coating the teat reduces the risk of bacteria colonising the mammary gland.

Products currently used for teat dipping contain a variety of different active ingredients such as iodophors, chlorhexidine and the lanthionine containing peptide, nisin.

Teat dip protocol:

To evaluate the potential of micrococcin as a prophylactic agent in bovine mastitis, the following experimental protocol can be used.

About 50 cattle are recruited according to the protocol already described for trials of these agents in therapy of subclinical staphylococcal mastitis. This trial then proceeds according to protocol recognised by the US National Mastitis Council (NMC) (Hogan et al. 1990) for testing efficacy of teat germicides during experimental exposure.

Throughout the trial period all teats are dipped in a challenge bacterial suspension after the evening milking on week days. Challenge suspensions contains $15 \times 10^7$ *Staphylococcus aureus* and $5 \times 10^7$ *Streptococcus agalactiae*. They are prepared each day from stock suspensions that are made up weekly. Aliquots of challenge suspension are plated each day to determine the real bacterial concentration present at the time of challenge.

After each milking the left fore and right hind teats are dipped in the test preparation of germicide, the other two teats remain as negative controls and are not dipped.

Foremilk samples of all quarters, for bacteriological culture, are taken twice weekly throughout the trial period. Any quarter, from which either challenge organism is isolated, is resampled within 48 hours. If the same organism is isolated then the quarter is considered infected. Similarly, an episode of clinical mastitis caused by either challenge organism is considered as a new intramammary infection.

Trials typically last from 3 to 6 months. At the end of the trial period the number of new intramammary infections between treatment groups is compared.

Example 5
Evaluation of reaction kinetics of DelvotestP in milk from quarters treated with micrococcin P1

To evaluate the potential effects of micrococcin P1 on strains of bacteria used in cheese and yoghurt manufacture the following experiment can be performed.

Delvotest P is a commercially available, widely used, kit for detection of antimicrobial agents in milk. It relies on the inhibition of growth of the indicator bacterium Bacillus stearothermophilus. The bacteria are suspended in an agar plug in a plastic test tube together with a pH indicator. Growth of bacteria results in acid production and colour change. In the presence of inhibiting substances the bacteria do not grow and there is no colour change. Bacillus stearothermophilus is a good representative of bacteria used in cheese and yoghurt manufacture and therefore it is widely used as an indicator strain in antibiotic residue detection.

During and after the administration of various treatments, samples are taken and they are evaluated using Delvotest P, as directed in the manufacturers recommendations. This sampling goes on until all treated quarters show a negative response.

TABLE 4

Results of Delvotest P in milk from bovine mammary gland quarters treated with different concentrations of micrococcin
The delvotest data are as follows

| [mg] of micrococcin- | No of quarters treated | treatment regime | no of milkings after last treatment that Delvotest P pos or +/- |
|---|---|---|---|
| 0 | 4 | 3 at 12 hrs | 0 |
| 0.5 | 4 | 3 at 12 hrs | 0 |
| 1 | 4 | 3 at 12 hrs | 1 |

TABLE 4-continued

Results of Delvotest P in milk from bovine mammary gland quarters treated with different concentrations of micrococcin
The delvotest data are as follows

| [mg] of micrococcin- | No of quarters treated | treatment regime | no of milkings after last treatment that Delvotest P pos or +/- |
|---|---|---|---|
| 2 | 4 | 3 at 12 hrs | 1 |
| 4 | 4 | 3 at 12 hrs | 2 | these data indicate that the dose of 0,5 mg of micrococcin does not interfere with Delvotest P.

Example 6
Evaluation of the direct effect on cheese and yoghurt manufacture of treatment of mammary gland quarters with different doses of antimicrobial agents in cheese and yoghurt manufacture different strains of bacteria are fermented in milk and one of the most important and immediate changes resulting from this fermentation is acid production. This acid is responsible for the control of secondary bacterial growth that could cause spoilage of the product or worse, illness in the consumer. Further fermentation of the lactic acid producing bacterial population produces changes in the cheese that vary with the strains of the bacteria used and the manufacturing methods. These factors are responsible for the physical characteristics and the flavour of different cheeses.

Acidification is the first and most important step in the manufacturing processes when milk is fermented. If acidification proceeds normally then it is very likely that all other steps will be normal. Therefore one can investigate the effect of different concentrations of micrococcin P1 on the kinetics of acidification of milk by lactic fermenting bacteria.

Experiments are routinely performed using one of the following strains of bacteria:
Streptococcus thermophilus
Lactobacillus bulgaricus Cows that are free from infection with mastitis pathogens, based on bacteriological culture of milk, are enrolled in these trials. Identical treatments are administered to all 4 quarters of an individual cow. Milk from evening milkings is refrigerated at 4° C. overnight to be tested the following morning. Samples of 500 ml are pasteurized by heating to 80° C. in a waterbath and then cooled to room temperature.

Lyophilised cultures as used in commercial conditions are obtained from Rudolf Wittwer, CH-5002 Rombach, Aarau, Switzerland. These cultures are reconstituted according to manufacturers recommendations and reactivated by passage three times in sterile skimmed milk. Each passage is incubated for 16 to 18 hours at the optimum temperature for the said bacterial strain.

The culture obtained after the third passage is diluted to 2% with whole sterile (UHT) milk, aliquotted in 10 ml tubes and frozen at −20° C. for use in experiments.

The stock cultures prepared above are thawed at 40° C. then incubated overnight at 37° C. and used to inoculate test samples. The test samples are inoculated with 2% by volume of the experimental culture of the bacterial strain under test. The samples are then mixed and incubated for 24 hours at the optimal temperature for the particular bacterial strain under evaluation. The pH is measured each two hours during an eight hour period and again at 24 hours. The rate of acidification of milk containing different concentrations of active micrococcin P1 can then be compared to the negative controls.

The results given in tables 4 and 5 below have been obtained from cows receiving various amounts of micrococcin P1 on three occasions, at 12 hour intervals. The doses are indicated in the table. The results demonstrate acidification of milk derived from the milking following administration of the last of the three doses.

TABLE 5

Acidification of milk by *Lactobacillus bulgaricus*

| hours of growth | 0 mg micrococcin P1 | 0.1 mg micrococcin P1 | 0.5 mg micrococcin P1 | 1 mg micrococcin P1 | 2 mg micrococcin P1 |
|---|---|---|---|---|---|
| 0 | 6.60 | 6.48 | 6.53 | 6.56 | 6.57 |
| 2 | 5.67 | 5.73 | 5.36 | 5.83 | 5.69 |
| 4 | 4.30 | 4.29 | 4.21 | 4.34 | 4.34 |
| 6 | 3.95 | 3.89 | 3.85 | 3.94 | 3.92 |
| 8 | 3.75 | 3.72 | 3.72 | 3.75 | 3.75 |
| 24 | 3.50 | 3.51 | 3.47 | 3.50 | 3.49 |

TABLE 6

Acidification of milk by *Streptococcus thermophilus*

| hours of growth | 0 mg micrococcin P1 | 0.1 mg micrococcin P1 | 0.5 mg micrococcin P1 | 1 mg micrococcin P1 | 2 mg micrococcin P1 |
|---|---|---|---|---|---|
| 0 | 6.68 | 6.60 | 6.61 | 6.67 | 6.72 |
| 2 | 5.91 | 6.03 | 6.04 | 6.20 | 6.33 |
| 4 | 4.52 | 4.47 | 4.50 | 4.53 | 4.74 |
| 6 | 4.11 | 4.08 | 4.13 | 4.11 | 4.25 |
| 8 | 3.96 | 3.94 | 4.00 | 3.94 | 4.06 |
| 24 | 3.52 | 3.52 | 3.51 | 3.48 | 3.57 |

REFERENCES

Hogan, J. S., Galton, D. M., Harmon, R., Nickerson, S. C., Oliver, S. P., Pankey, J. W. (1990) Protocols for Evaluating efficacy of postmilking teat dips. J. Dairy Sci. 73 pp 2580–2585.

Philpot, W. N., (1984) Economics of mastitis control, Veterinary Clinics of North America: Large Animal Practice 6(2) pp 233–245.

Cullor, J. S., Tyler, J. W., Smith, B. P. (1990) Disorders of the mammary gland in large animal medicine, B. P. Smith, The C. V. Mosby Company, St Louis, Mo. 63146, USA., pp 1047–1067.

Bycroft et al, (1978) The structures of the highly modified peptide antin^biotics Micrococcin P1 and P2. J.C.S. Chem. Comm.: pp256–258, J. Berdy, A. Aszalos M. Bostian K. L. McNitt (1980). CRC Handbook of Antibiotic Compounds,Amino acid and Peptide Antibiotics CRC Press Boca Raton Fl USA 4 (1) pp.-389–417.

We claim:

1. A method of treating or preventing contagious mastitis caused by pathogens susceptible to micrococcin P1 or P2 in a mammal comprising administering to the mammal a therapeutically effective amount of micrococcin P1 or P2, wherein the milk obtained from the mammal after the administration of the micrococcin P1 or P2 is suitable for use in the production of cheese or yogurt.

2. The method according to claim 1 comprising continuous or multiple administration of said antibiotic.

3. The method according to claim 2 wherein the administration of the antibiotic is to a mammal selected from the group consisting of a cow, a goat and a ewe.

4. The method according to claim 1 comprising administration of the antibiotic either by intramammary injection or by teat dipping.

5. The method according to claim 4 wherein the administration of the antibiotic is to a mammal selected from the group consisting of a cow, a goat and a ewe.

6. The method according to claim 1, wherein said mammal is a cow, goat or ewe.

7. The method for combating contagious mastitis in a mammal according to claim 1 comprising administering to the mammal from about from about 0.1 mg/kg to about 200 mg/kg of micrococcin P1 or P2, wherein the milk obtained from the mammal after administration of said micrococcin P1 or P2 is suitable for use in the production of cheese or yogurt.

8. A method for the prophylaxis of contagious mastitis in a mammal comprising administering to the mammal a therapeutically effective amount of micrococcin P1 or P2, wherein the milk obtained from the mammal after the administration of the micrococcin P1 or P2 is suitable for use in the production of cheese or yogurt.

9. A method for the preparation of micrococcin P1 or P2 comprising fermenting the bacterial species *Staphylococcus sciuri* according to standard techniques, sterilizing the whole fermentation broth, separating the bacterial cells from the fermentation broth, and extracting micrococcin P1 or P2 from the cells with methanol.

* * * * *

UNITED STATES PATENT AND TRADEMARK OFFICE
CERTIFICATE OF CORRECTION

Page 1 of 1

PATENT NO. : 6,187,800 B1
DATED : February 13, 2001
INVENTOR(S) : Suri et al.

It is certified that error appears in the above-identified patent and that said Letters Patent is hereby corrected as shown below:

<u>Title page,</u>
Left column, section (30) should read:

(30) Foreign Application Priority Data

June 20, 1996 (DE)......................................................96810415.8

Signed and Sealed this

Eleventh Day of September, 2001

*Attest:*

*Attesting Officer*

NICHOLAS P. GODICI
*Acting Director of the United States Patent and Trademark Office*